US00PP37033P3

(12) United States Plant Patent
Cline

(10) Patent No.: US PP37,033 P3
(45) Date of Patent: Oct. 21, 2025

(54) CRAB APPLE TREE NAMED 'B17Crab7'

(50) Latin Name: ***Malus sylvestris* L.**
Varietal Denomination: B17Crab7

(71) Applicant: University of Guelph, Guelph (CA)

(72) Inventor: John A. Cline, Grimsby (CA)

(73) Assignee: University of Guelph, Guelph (CA)

( * ) Notice: Subject to any disclaimer, the term of this patent is extended or adjusted under 35 U.S.C. 154(b) by 0 days.

(21) Appl. No.: 18/830,279

(22) Filed: Sep. 10, 2024

(65) Prior Publication Data

US 2024/0431221 P1 Dec. 26, 2024

Related U.S. Application Data

(63) Continuation-in-part of application No. 18/111,626, filed on Feb. 20, 2023, now abandoned.

(51) Int. Cl.
*A01H 5/08* (2018.01)
*A01H 6/74* (2018.01)

(52) U.S. Cl.
USPC ..... Plt./173
CPC ..... *A01H 6/7418* (2018.05)

(58) Field of Classification Search
USPC ..... Plt./156, 161, 173
See application file for complete search history.

(56) References Cited

U.S. PATENT DOCUMENTS

2024/0276940 A1* 8/2024 Cline ..... A01H 5/08

OTHER PUBLICATIONS

Carroll, R. 2022. 'Providence' Crab Apple. University of Geulph: Research Innovation. chrome-extension://efaidnbmnnnibpcajpcglclefindmkaj/https://www.uoguelph.ca/research/innovation/sites/default/files/Tech_Transfer/US_MarketSheet_ProvidenceCrabApple_Feb.2022.pdf (Year: 2022).*
Research Innovation Office at UofG. 2021. https://x.com/CreatedAtGuelph/status/1348716397963210753 (Year: 2021).*

* cited by examiner

*Primary Examiner* — Karen M Redden
(74) *Attorney, Agent, or Firm* — Weatherly IP Solutions, LLC; James Weatherly

(57) ABSTRACT

A new crab apple tree particularly distinguished by fruit with a distinct ellipsoid conical (ovoid) shape, long pedicel that is red (stem), and range in weight from 20-45 g. The fruit have a predominantly dark red, reddish-purple skin colour and cherry coloured red flesh. When pressed, crimson red juice is extracted that is high in acidity and polyphenols. The tree is moderately vigorous, red leaves at bloom that turn dark green during development. Flowers are pink in color when fully open. The shoots have a distinctly red colour which is clearly distinguishable from other apple cultivars, is disclosed.

3 Drawing Sheets

CROSS REFERENCE TO RELATED APPLICATION

The present application is a continuation in part of and claims priority to U.S. application Ser. No. 18/111,626, as filed on Feb. 20, 2023, the entire contents of which are incorporated herein by reference for all purposes.

Genus and species: *Malus sylvestris* L.

Variety denomination: 'B17Crab7'.

BACKGROUND OF THE NEW PLANT

The present invention comprises a new and distinct variety of crab apple, botanically known as *Malus sylvestris* L. and hereinafter referred to by the variety name 'B17Crab7'. 'B17Crab7' originated from an open pollinated cross conducted in 2000 between the female parent variety 'Empire' (unpatented) and an unknown male parent. It was bred and developed in Simcoe, Ontario, Canada. The resulting seeds were germinated in 2001 and transplanted in an orchard in 2002. One resulting seedling of 'B17Crab7' was selected for its fruit qualities such as showy bloom, and large fruit with red flesh. The selected seedling was asexually propagated onto clonal M.26 rootstock (unpatented) for further evaluation. Trees were then planted in 2007 in replicated and randomized fashion of two trees per plot with other crab apple selections as well as the reference cultivars for further evaluation in 2007.

'B17Crab7' has shown uniformity and stability, as described in the following variety description information. Crab apple cultivar 'B17Crab7' was tested for uniformity and stability a sufficient number of generations with careful attention to uniformity of plant type and has been increased with continued observation for uniformity.

SUMMARY

The following are the most outstanding and distinguishing characteristics of this new variety when grown under normal horticultural practices in Simcoe, Ontario, Canada.

1. The fruit of 'B17Crab7' have a distinct ellipsoid conical (ovoid) shape, long pedicel that is red (stem), and range in weight from 20-45 g;
2. The fruit have a predominantly dark red, reddish-purple skin colour and cherry coloured red flesh;
3. When pressed, crimson red juice is extracted that is high in acidity and polyphenols;

4. The tree is moderately vigorous, red leaves at bloom that turn dark green during development;
5. Flowers are pink in color when fully open; and
6. The shoots have a distinctly red colour which is clearly distinguishable from other crab apple cultivars.

DESCRIPTION OF THE PHOTOGRAPHS

This new crab apple tree is illustrated by the accompanying photographs from October 2023 of four year old plants grown in Simcoe, Ontario, Canada. The colors shown are as true as can be reasonably obtained by conventional photographic procedures.

DESCRIPTION OF THE NEW VARIETY

Figure 1:
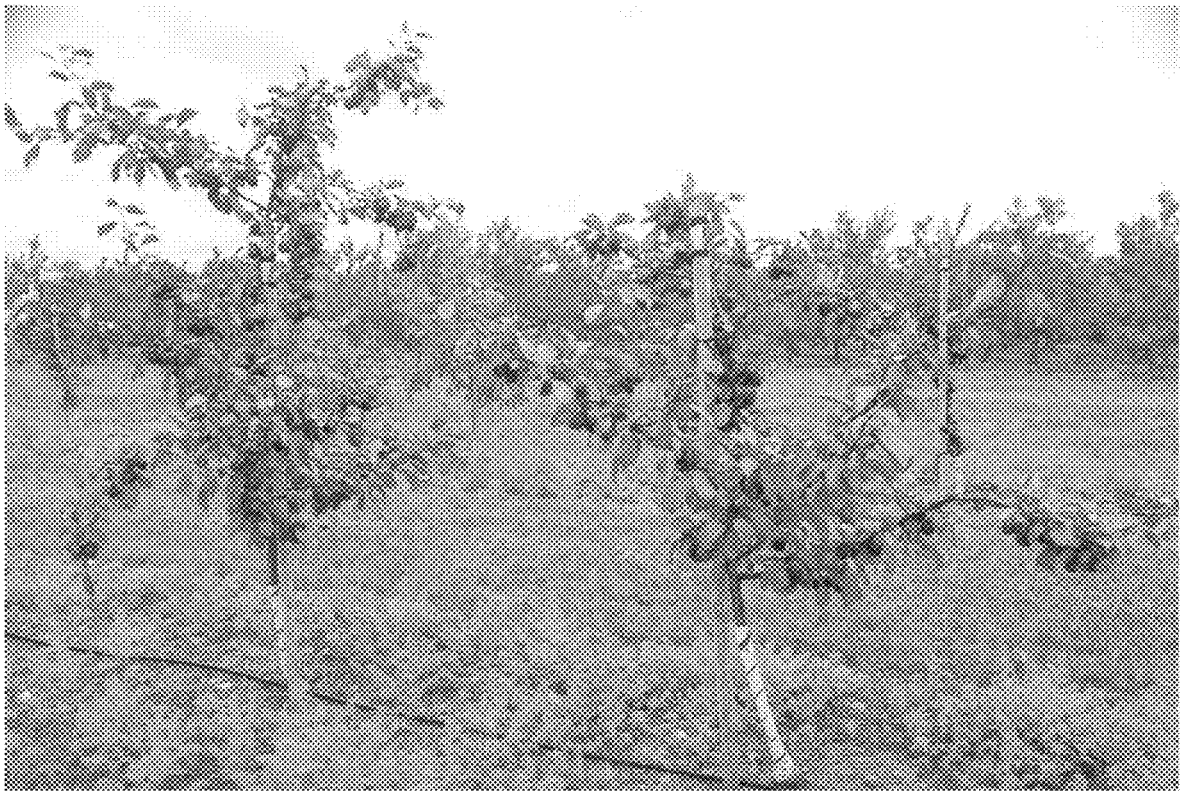
FIG. 1 shows a whole tree of 'B17Crab7' showing foliage and fruit.
Figure 2:
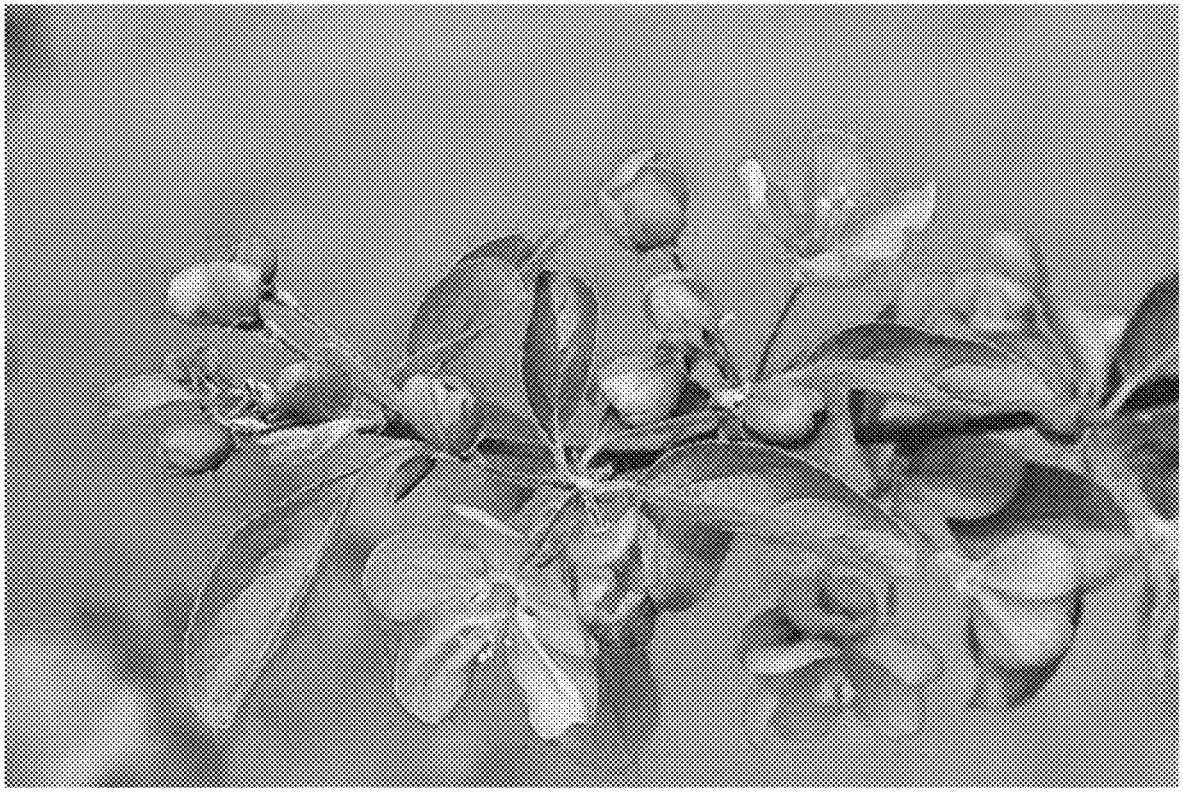
FIG. 2 shows the leaves, buds and flowers of 'B17Crab7'.
Figure 3:
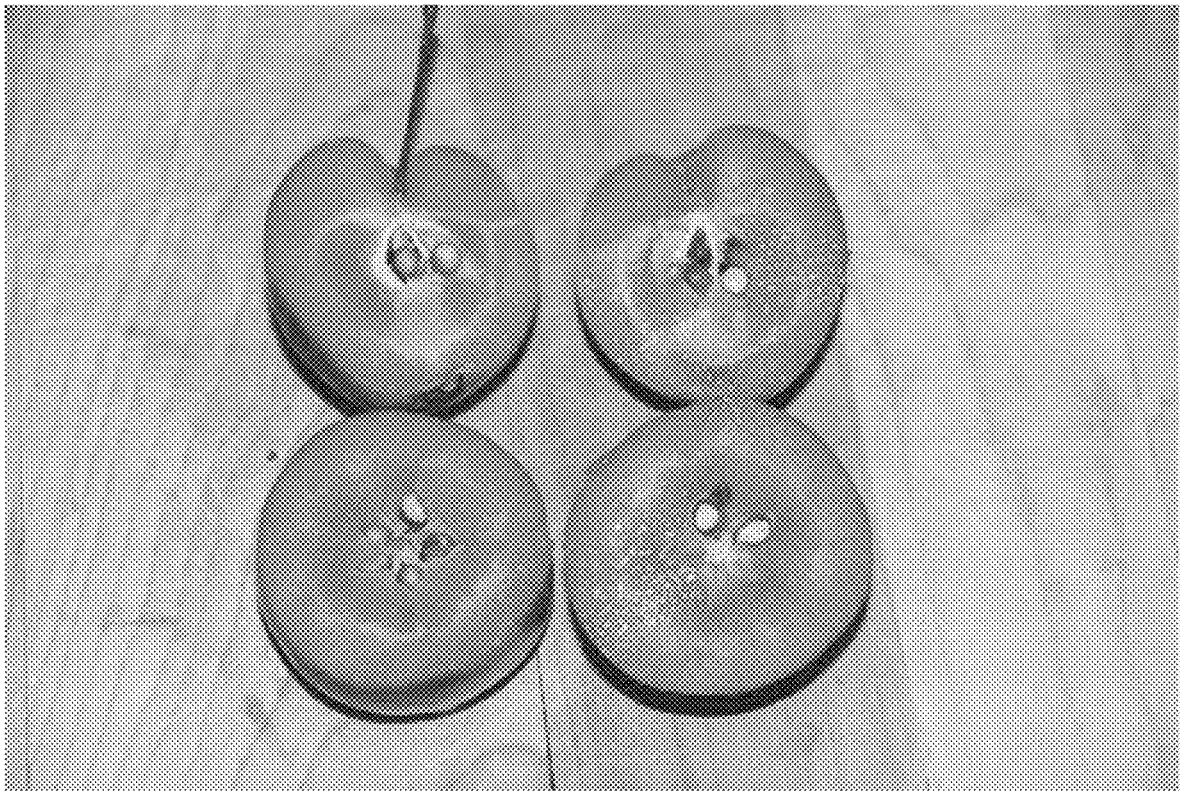
FIG. 3 shows the flesh and seeds of the fruit of 'B17Crab7'.

The following detailed descriptions set forth the distinctive characteristics of 'B17Crab7'. The data which define these characteristics was collected in Simcoe, Ontario on two year old and nine year old trees. All colour determinations were made using 2015 Royal Horticultural Society (R.H.S.) Colour Chart.

Classification:

*Family*.—Rosaceae.

*Species*.—*Malus sylvestris* L.

*Denomination*.—'B17Crab7'.

General:

*Overall shape*.—Spreading.

*Vigour*.—Medium to strong vigour with many fruit.

*Height*.—3.34 M (9 years old).

*Width*.—2.02 M (9 years old).

*Market use*.—Cider, jams and jellies (food products), and ornamental.

*Hardiness*.—Plants will survive in USDA zone 6b.

*Disease resistance*.—Unknown.

Trunk:

*Diameter*.—7.45 cm (9 years old).

*Bark texture/surface appearance*.—Young: Rough (2 years old). Mature: Rough (9 years old).

*Bark color*.—Young: RHS 183A (2 years old). Mature: RHS 177A (9 years old).

*Lenticels*.—Color: RHS 162A. Shape: Ellipse. Size: Length: 3.0 mm. Width: 1.0 mm.

Branches: (9 years old).

*Length*.—120.33 cm.

*Width*.—4.5 cm.

*Shape in cross-section*.—Spreading.

*Color, young branches*.—RHS 200B.

*Color, mature branches*.—RHS 177A.

*Lenticels*.—Color: RHS 164C. Shape: Oval. Size: Length: 1.0 mm. Width: 0.5 mm.

*Dormant buds*.—Shape: Cylindrical, Pointed. Apex: Pointed. Base: Wide, flat. Color: RHS 166A. Internode length: 4.0 cm, 9 years old.

Foliage: (9 years old).

*General*.—Medium length to width ratio, no lobing, crenate type incisions of margin, mainly red before leaf fall.

*Quantity of leaves per branch*.—Various with branch length and age.

*Arrangement and type*.—Alternate, simple.

*Length*.—9.87 cm.

*Width*.—5.86 cm.

*Shape*.—Ovate.

*Apex*.—Pointed.

*Base*.—Round.

*Margin*.—Crenulate.

*Texture, immature*.—Upper surface: Smooth. Lower surface: Smooth.

*Color, immature*.—Upper surface: Medium Pink (RHS 59A), strong intensity of anthocyanin coloration. Lower surface: RHS 59B.

*Texture, mature*.—Upper surface: Medium glossiness (smooth). Lower surface: Smooth.

*Color, mature*.—Upper surface: RHS NN137B. Lower surface: RHS 137D (greenish brown).

*Venation pattern*.—Pinnate.

*Venation color, mature*.—Upper surface: RHS 137B. Lower surface: RHS 58A (reddish/purple). Petioles: Color: RHS 183B. Length: 3.29 mm. Width: 0.94 mm. Stipules: Not observed.

Flowers: (9 years old).

*Type*.—single type, medium pink (RHS 59C) on outer side at balloon stage, flat, overlapping petal arrangement.

*Flowering date*.—May 15 (on average in Simcoe, Ontario).

*Fragrance*.—Not observed.

*Number of flowers per cluster*.—5.

*Shape of flowers*.—Flat, overlapping arrangement.

*Bud*.—Length: 8.8 mm (average of 10 buds). Width: 5.2 mm (average of 10 buds). Bud color: RHS 145D.

Petals: (9 years old).

*Quantity per flower*.—5.

*Shape*.—Ovate, excluding claw.

*Apex*.—Round.

*Base*.—Pointed.

*Margin*.—Entire (smooth).

*Length*.—6.14 cm.

*Width*.—3.29 cm.

*Color*.—Upper surface: RHS 59C on marginal and middle zone, RHS NN155D on Basal Zone. Lower surface: RHS 59C.

*Surface texture*.—Upper surface: Smooth, no prominent veins. Lower surface: Smooth, no prominent veins.

Sepals: (9 years old).

*Quantity per flower*.—5.

*Apex*.—Pointed.

*Base*.—Round.

*Margin*.—Smooth, non serrated.

*Length*.—3.7 mm.

*Width*.—2.4 mm.

*Color*.—Upper surface: RHS 160C and RHS 183C. Lower surface: RHS 160D.

*Surface texture*.—Upper surface: Fuzzy. Lower surface: Fuzzy.

*Pedicel*.—Color: RHS N138C. Length: 13.03 mm. Width: 1.02 mm.

Reproductive organs: (9 years old).

*Stamens*.—Stamen quantity per flower: 17. Filament length: 6.4 mm. Anther color: RHS 166C for older stamens, RHS 162D for new.

*Pollen amount*.—Not Observed.

*Pistils*.—Stigma shape: Lobed. Stigma color: RHS 151C. Style length: 4.12 mm. Style color: RHS 151D.

*Ovary color*.—RHS 196B.

*Ovary shape*.—Oblong.

Fruit: (9 years old).

*Number of fruits per cluster*.—3-5.

*Stalk*.—Long.

*Size*.—Small (20-45 g) (when the trees are not thinned).

*Shape*.—Ellipsoid Conical.

*Skin texture*.—Smooth, non-glossy.

*Skin color*.—RHS 59A or RHS 187B (blush); RHS 53A and RHS 186C (ground).

*Flesh color*.—RHS 46B or RHS 53B (Range).

*Seeds*.—Reddish/brown.

*Fruit production*.—Heavy.

COMPARISON WITH PARENTAL LINE AND KNOWN VARIETY

'B17Crab7' is distinguished from its female parent as described in Table 1.

TABLE 1

| Comparison with Female Parent | | |
|---|---|---|
| Characteristic | 'Empire' | 'B17Crab7' |
| Fruit surface colour | Red skin with green background colour | Red skin |
| Fruit Shape | globose | ellipsoid conical (ovoid) shape |
| Flesh colour | White | Red |
| Fruit size | 100-150 g | 30-40 g |
| Fruit flavour | Sweet with mild acidity | Tart, high acidity |

TABLE 1-continued

| Comparison with Female Parent | | |
|---|---|---|
| Characteristic | 'Empire' | 'B17Crab7' |
| Tree leaf colour | Green | Red early in the season, turning green |
| Flower colour | White | Pink |
| Juice colour | Clear | Crimson red |
| Pedicel length | Relatively short | Relatively long |
| Tree habit | Spreading | Spreading to drooping |

Table 2 below shows trials for 'B17Crab7' were conducted from 2014 to 2017 in Simcoe, Ontario. The trials consisted of 7 trees of 'B17Crab7', grown on M.26 rootstock (unpatented), and five trees of 'Kerr', (unpatented) grown on Bud.9 rootstock (unpatented). In 2014, the trees were planted in 86 metre length rows, with 4.5 metre spacing between rows and 2 metres between trees. Mean differences were significant at the 5% confidence probability level based on a paired Student's t-test.

TABLE 2

| Characteristics | 'B17Crab7' | 'Kerr' |
|---|---|---|
| Petiole length | 3.29 cm | 1.90 cm |
| Leaf blade length mean | 9.87 cm | 6.92 cm |
| Leaf blade width mean | 5.86 cm | 3.99 cm |
| Flower diameter | 6.14 cm | 4.6 cm |
| Color of flower petal | RHS 59C | RHS NN155D |

I claim:

1. A new and distinct variety of crab apple tree designated 'B17Crab7' as illustrated and described herein.

* * * * *